US006759402B2

(12) United States Patent
Macdonald et al.

(10) Patent No.: US 6,759,402 B2
(45) Date of Patent: Jul. 6, 2004

(54) CYCLIC FELBAMATE DERIVED COMPOUNDS

(75) Inventors: Timothy L. Macdonald, Charlottesville, VA (US); Thomas A. Miller, New York, NY (US); Charles D. Thompson, Stow, MA (US); Christine M. Dieckhaus, North Wales, PA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 10/456,117

(22) Filed: Jun. 6, 2003

(65) Prior Publication Data

US 2003/0229086 A1 Dec. 11, 2003

Related U.S. Application Data

(62) Division of application No. 10/023,059, filed on Dec. 17, 2001, now Pat. No. 6,599,935, which is a continuation of application No. 09/913,075, filed as application No. PCT/US00/03147 on Feb. 8, 2000, now abandoned, said application No. 10/023,059, is a continuation of application No. 09/925,224, filed on Aug. 9, 2001, now Pat. No. 6,538,024, which is a continuation of application No. PCT/US00/03147, filed on Feb. 8, 2000.
(60) Provisional application No. 60/119,254, filed on Feb. 9, 1999, provisional application No. 60/136,881, filed on Jun. 1, 1999, and provisional application No. 60/137,204, filed on Jun. 2, 1999.

(51) Int. Cl.$^7$ .................. A61K 31/33; A61K 31/42; A61K 31/27; C07D 265/04; C07D 263/00

(52) U.S. Cl. ............... 514/183; 514/228.8; 514/374; 514/376; 514/478; 544/88; 544/97; 548/215; 548/225; 548/229

(58) Field of Search .................. 514/228.8, 374, 514/376, 478, 183; 544/88, 97; 548/215, 225, 229

(56) References Cited

U.S. PATENT DOCUMENTS

| 2,884,444 A | | 4/1959 | Berger et al. | |
|---|---|---|---|---|
| 4,161,582 A | * | 7/1979 | Weigele et al. | ............... 536/23 |
| 4,384,115 A | * | 5/1983 | Renga | ......................... 544/97 |
| 4,868,327 A | | 9/1989 | Stiefel | |
| 4,978,680 A | | 12/1990 | Sofia | |
| 5,055,489 A | | 10/1991 | Sofia | |
| 5,082,861 A | | 1/1992 | Sofia | |
| 5,292,772 A | | 3/1994 | Sofia | |
| 5,462,966 A | | 10/1995 | Sofia | |
| 5,492,930 A | | 2/1996 | Coffin | |

FOREIGN PATENT DOCUMENTS

| WO | WO-94/06737 | 3/1994 |
|---|---|---|
| WO | WO-97/37652 | 10/1997 |

OTHER PUBLICATIONS

Cecil's Textbook of Medicine, 20$^{th}$ Edn.,vol.2,pp. 1992–1996.*
Zink et al,PubMed.Abstract 14500177,also cited as Anesth.Analg.,97/4,1173–9(2003).*
Wu et al, PubMed Abstract 9784280, also cited as Exp. Neurol.,153/2,203–13(1998).*
Lallement et al, PubMed Abstract 9342591, also cited as Fundam. Clin. Pharmacol.,11/5,387–94(1997).*
Rubaj et al, PubMed Abstract 12479949, also cited as Pharmacol. Biochem. Behav.,74/2,303–11(2003).*
Chabrier et al, PubMed Abstract 10442086, also cited as Cell. Mol. Life Sci.,55/8–9.1029–35(1999).*
M. G. O'Neil, et al., "Felbamate–associated fatal acute hepatic necrosis," Neurology, 46, pp. 1457–1459, (May 1996).
Y. M. Choi, et al., "Metabolites of Felbamate: Synthesis of 2-(4-Hydroxyphenyl)-1,3-Propanediol Dicarbamate, 2-Phenyl-2-Hydroxy-1, 3-Propanediol Dicarbamate, and 2-Phenyl-1,3-Proanediol Monocarbamate," Tetrahedron, 42 (23), pp. 6399–6404, (1986).
P. B. Pennell, et al., "Aplastic anemia in a patient receiving felbamate for complex partial seizures," Neurology, 45, pp. 456–460, (Mar. 1995).
Adusumalli, V.E., et al., "Isolation and Identification of 3–Carbamoyloxy–2–Phenylpropionic Acis as a Major Human Urinary Metabolite of Felbamate", The American Society for Pharmacology and Experimental Therapeutics, vol. 21, pp. 710–716, (1993).
Burdette, D.E., et al., "Felbamate Pharmacology and Use in Epilepsy", Clinical Neuropharmacology, vol. 17, No. 5., pp. 389–402, (1994).
Kapetanovic, I.M., et al., "Potentially Reactive Cyclic Carbamate Metabolite of the Antiepileptic Drug Felbamate Produced by Human Liver Tissue In Vitro", The American Soc. for Pharmacology and Experimental Therapeutics, vol. 26, No. 11, pp 1089–1095 (1998).
Kaufman, D.W., et al., "Evaluation of Case Reports of Aplastic Anemia Among Patients Treated with Felbamate", Epilipsia, 38 (12), pp. 1265–1269 (1997).
Schmidt, D., "Felbamate: Successful Development of a New Compound for the Treatment of Epilepsy", Epilepsia, 34(Suppl. 7), pp. S30–S33 (1993).
Shuaib, A., et al., "Neuroprotection with Felbamate: A7–and 28–Day Study in Transient Forebrain Ischemia in Gerbils", Brain Research 727, pp. 65–70, (1996).

(List continued on next page.)

Primary Examiner—Richard L. Raymond
Assistant Examiner—Sudhaker B. Patel
(74) Attorney, Agent, or Firm—John P. Breen

(57) ABSTRACT

The present invention relates to novel felbamate derivatives and their use to treat neurological diseases such as epilepsy and to treat tissue damage resulting form ischemic events. The felbamate derivatives are modified to prevent the formation of metabolites that are believed responsible for the toxicity associated with felbamate therapy.

30 Claims, No Drawings

OTHER PUBLICATIONS

Sofia, R.D., "Mechanism of Action of the Anticonvulsant Felbamate: Opposing Effects on N–Methyl–D–Aspartae and", American Neurological Association, pp. 677–678, (1994).

Wamsley, J.K. et al., "Interaction of Felbamate with [3H] DCKA–Labeled Strychnine–Insensitive Glycine Receptors in Human Postmortem Brain", Experimental Neurology 129, 244–250, (1994).

Yang, J.T., et al., "Felbamate Metabolism in the Rat, Rabbit, and Dog", American Society for Pharmacology and Experimental Therapeutics, vol. 19, No. 6, pp. 1126–1134 (1991).

Knight, J.L., et al., "A Computational Quantitative Structure—Activity Relationship Study of Carbamate Anticonvulsants Using Quantum Pharmacological Methods", Seizure, 347–354, (1998).

Sheilds, W.D., "Investigational Antiepileptic Drugs for the Treatment of Childhood Seizure Disorders: a Review of Efficacy and Safety", Epilepsia, 24–29 (1994) )Abstract Only).

* cited by examiner

CYCLIC FELBAMATE DERIVED COMPOUNDS

This application is a divisional of U.S. Ser. No. 10/023,059, filed Dec. 17, 2001 now U.S. Pat. No. 6,599,935, which is a continuation of U.S. Ser. No. 09/913,075, filed Aug. 9, 2001 now abandoned, which is a 35 USC § 371 national stage application of PCT/US00/03147, filed on Feb. 8, 2000. U.S. Ser. No. 10/023,059 is also a continuation of U.S. Ser. No. 09/925,224, filed Aug. 9, 2001, now U.S. Pat. No. 6,538,024 issued on Mar. 25, 2003, which is a continuation of International Patent Application No. PCT/US00/03147, filed on Feb. 8, 2000. This application also claims priority under 35 U.S.C. § 119(e) to U.S. Provisional Patent Application Nos. 60/119,254, 60/136,881 and 60/137,204, filed on Feb. 9, 1999, Jun. 1, 1999 and Jun. 2, 1999, respectively. The disclosures of all the above priority documents are incorporated herein by reference in their entirety.

FIELD OF THE INVENTION

The present invention is directed to novel derivatives of 2-phenyl-1,3-propanediol dicarbamate (felbamate), and the use of such derivatives as therapeutic agents. More particularly, compositions comprising the present felbamate derivatives can be administered for reducing the incidence and severity of epileptic seizures and for preventing and treating hypoxic damage resulting from an ischemic event.

BACKGROUND OF THE INVENTION

Felbamate (2-phenyl-1,3-propanediol dicarbamate) is a known pharmaceutical compound having been described in U.S. Pat. Nos. 2,884,444 and 4,868,327, the disclosures of which are expressly incorporated herein. Felbamate is a modulator of NMDA (N-methyl-D-aspartate) receptor function, and a glycine site antagonist but also has other reported mechanisms of actions.

Felbamate has also been reported to interact at the AMPA/kainate receptor, facilitate the function of the GABA receptor, and modulate Na.sup.+channel conductance. Felbamate has also been demonstrated to decrease delayed neuronal cell death after kainic acid induced status epilepticus in animals. Glycine or d-serine were able to functionally reverse the anticonvulsant and ischemic protective effect of felbamate.

Felbamate has been proposed for use in treating various neurological disorders including the control of epileptic seizures. For example, U.S. Pat. No. 4,978,680 discloses the use of felbamate for the prevention and control of epileptic seizures; U.S. Pat. No. 5,082,861 relates to the use of felbamate for the prevention and control of epileptic seizures associated with complex partial seizures; and U.S. Pat. No. 5,292,772 relates to the use of felbamate for the prevention and control of epileptic seizures associated with Lennox-Gastaut syndrome. The disclosures of U.S. Pat. Nos. 4,978,680, 5,082,861 and 5,292,772 are expressly incorporated herein.

Felbamate has also been reported to have efficacy in reducing cellular damage resulting from vascular reperfusion (U.S. Pat. No. 5,462,966) and preventing and treating tissue damage resulting from an ischemic event (U.S. Pat. No. 5,055,489). For example, compositions comprising felbamate can be administered to control or prevent hypoxic damage resulting form stroke and other cerebral ischemic events. The disclosure of U.S. Pat. Nos. 5,462,966 and 5,055,489 are also expressly incorporated herein.

Felbamate was approved in July 1993 for the treatment of several forms of epilepsy. Felbamate demonstrated an excellent therapeutic index throughout preclinical and clinical trials with only relatively mild side effects observed and/or reported. In its first year of approval, between 100,000 and 125,000 patients were placed on felbamate therapy in the U.S. However, within the first year of felbamate's wide spread use, adverse reactions were reported, notably aplastic anemia and hepatotoxicity. (See Pennell et al., *Neurology*. 45, 456–460 (1995) and O'Neil et al., *Neurology*. 46, 1457–1459 (1996)). The severity and frequency of occurrence of these side effects prompted a recommendation by the FDA in August 1994 to withdraw patients from felbamate therapy, unless the benefit of seizure control outweighed the risk of the reported toxicities.

The present invention is directed to felbamate derivatives, and their metabolites, that exhibit therapeutic properties similar to felbamate, without the adverse reactions observed with felbamate administration. In accordance with the present invention these felbamate derivatives are used to treat neurological disorders and prevent and/or control tissue damage resulting from hypoxic conditions. More particularly, the present novel compounds are believed to be useful for treating epileptic seizures and for preventing or alleviating cellular damaged caused by myocardial or cerebral ischemic events.

The presently disclosed derivatives of felbamate have been shown to have activity as neuroprotectants and are believed to have biological activities similar to those of the parent felbamate compound. However, the present compounds have been modified to prevent the formation of metabolites that are believed to cause the adverse reactions associated with the use of felbamate. Accordingly, it is anticipated that the felbamate derivatives of the present invention can be substituted for felbamate for all the therapeutic uses that have been proposed for felbamate. In addition, many of the derivatives have enhanced activities allowing for the administration of lower therapeutically effective dosage forms.

SUMMARY OF THE INVENTION

The present invention is directed to novel compounds of the general formula:

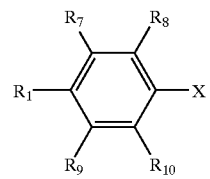

wherein X is selected from the group consisting of

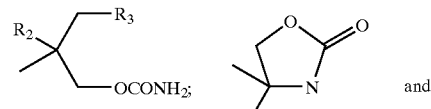

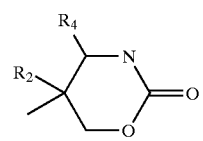

and $R_1$, $R_7$, $R_8$, $R_9$ and $R_{10}$ are independently selected from the group consisting of H, halo, alkyl, haloalkyl, —NR$_5$R$_6$, hydroxy, and alkoxy, R$_2$ is halo, R$_3$ is hydroxy or —OCONH$_2$, R$_4$ is hydroxy or carbonyl, and R$_5$ and R$_6$ are independently C$_1$–C$_4$ alkyl. These novel compounds are derivatives of felbamate; and in particular, the original felbamate structure has been modified to prevent the formation of metabolite 2-phenylpropenyl (atropaldehyde) upon administration to a warm blooded vertebrate. The formation of atropaldehyde is believed to be responsible for the adverse effects associated with the administration of felbamate. These felbamate derivatives exhibit similar activities to felbamate without the risk of the toxicities associated with felbamate administration. In accordance with the present invention compositions comprising a felbamate derivative are administered to a patient to provide neuroprotection in systemic and neurological disease and to treat tissue damage resulting from ischemic events. The compounds can be administered prophylactically, acutely, subacutely, or chronically via the intravenous, oral or rectal route.

DETAILED DESCRIPTION OF THE INVENTION

In describing and claiming the invention, the following terminology will be used in accordance with the definitions set forth below.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, "effective amount" means an amount sufficient to produce a selected effect. For example, an effective amount of a neuroprotective felbamate derivative is an amount of the active agent sufficient to significantly reduce the incidence and severity of epileptic seizures. An effective amount of a hypoxia ameliorating felbamate derivative is an amount of the active agent sufficient to prevent or significantly reduce cellular damage resulting from coronary artery occlusion/reperfusion or other hypoxia inducing event.

The general chemical terms used in the description of the compounds of the present invention have their usual meanings. For example, the term "alkyl" by itself or as part of another substituent means a straight or branched aliphatic chain having the stated number of carbon atoms.

The term "halo" includes bromo, chloro, fluoro, and iodo.

The term, "parenteral" means not through the alimentary canal but by some other route such as subcutaneous, intramuscular, intraspinal, or intravenous.

As used herein, the term "treating" includes alleviating the symptoms associated with a specific disorder or condition and/or preventing or eliminating said symptoms.

The following metabolic pathway (Scheme I) of felbamate (1) has been proposed that leads to the reactive metabolite, 3-carbamoyl-2-phenylpropionaldehyde (3).

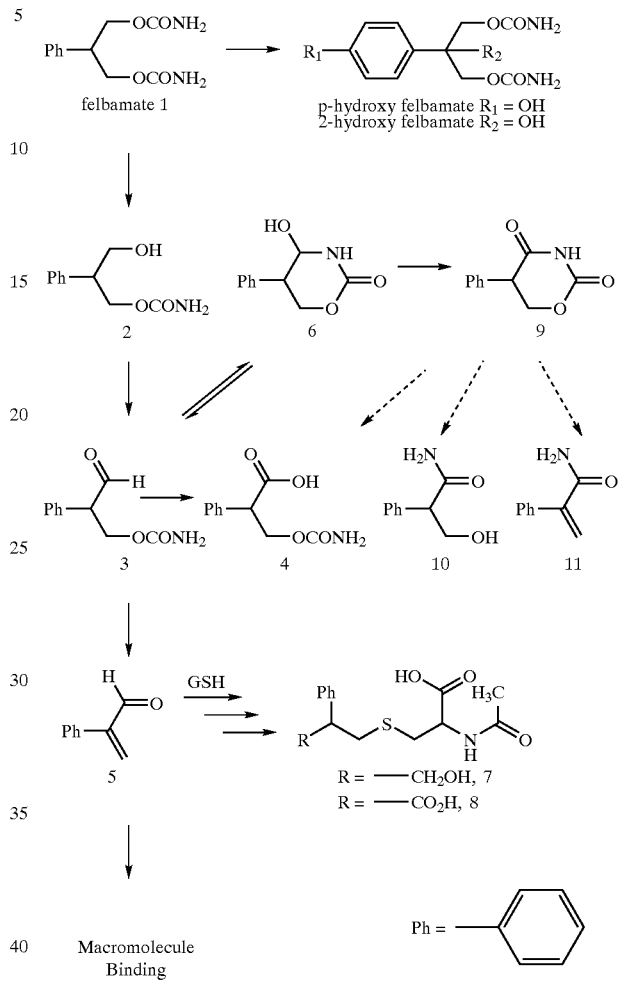

Scheme I
The metabolism of felbamate.

3-Carbamoyl-2-phenylpropionaldehyde (3) is believed to be a reactive intermediate in the oxidation of 2-phenyl-1,3-propanediol monocarbamate (2) to the major human metabolite 3-carbamoyl-2-phenylpropionic acid (4). In addition, the aldehyde carbamate (3) was found to undergo spontaneous elimination to form the α, β unsaturated aldehyde, 2-phenylpropenal (5), commonly known as atropaldehyde. Atropaldehyde has been proposed to play a role in the development of toxicity during felbamate therapy.

Evidence for atropaldehyde formation in vivo has been reported with the identification of modified N-acetylcysteine conjugates 7 and 8 of atropaldehyde in both human and rat urine after felbamate administration. Identification of the atropaldehyde derived mercapturic acids in urine after felbamate administration is consistent with the hypothesis that atropaldehyde is formed in vivo and that it reacts with thiol nucleophiles.

Based on the hypothesis that the toxicity associated with felbamate administration is directly correlated to the amount of atropaldehyde formed, the present invention is directed to the development of a new class of agents structurally related to felbamate that cannot undergo metabolism to atropaldehyde.

In accordance with the present invention the benzylic hydrogen of felbamate (1) is replaced with a substituent "$R_2$" as shown in the following metabolic scheme (Scheme II). $R_2$ is halo, and in one preferred embodiment the substituent is a fluorine atom.
Fluorofelbamate (12) and fluoro monocarbamate felbamate (13) are derivatives of known antiepileptic agents. These agents represent a new class of anti-epileptics that, while
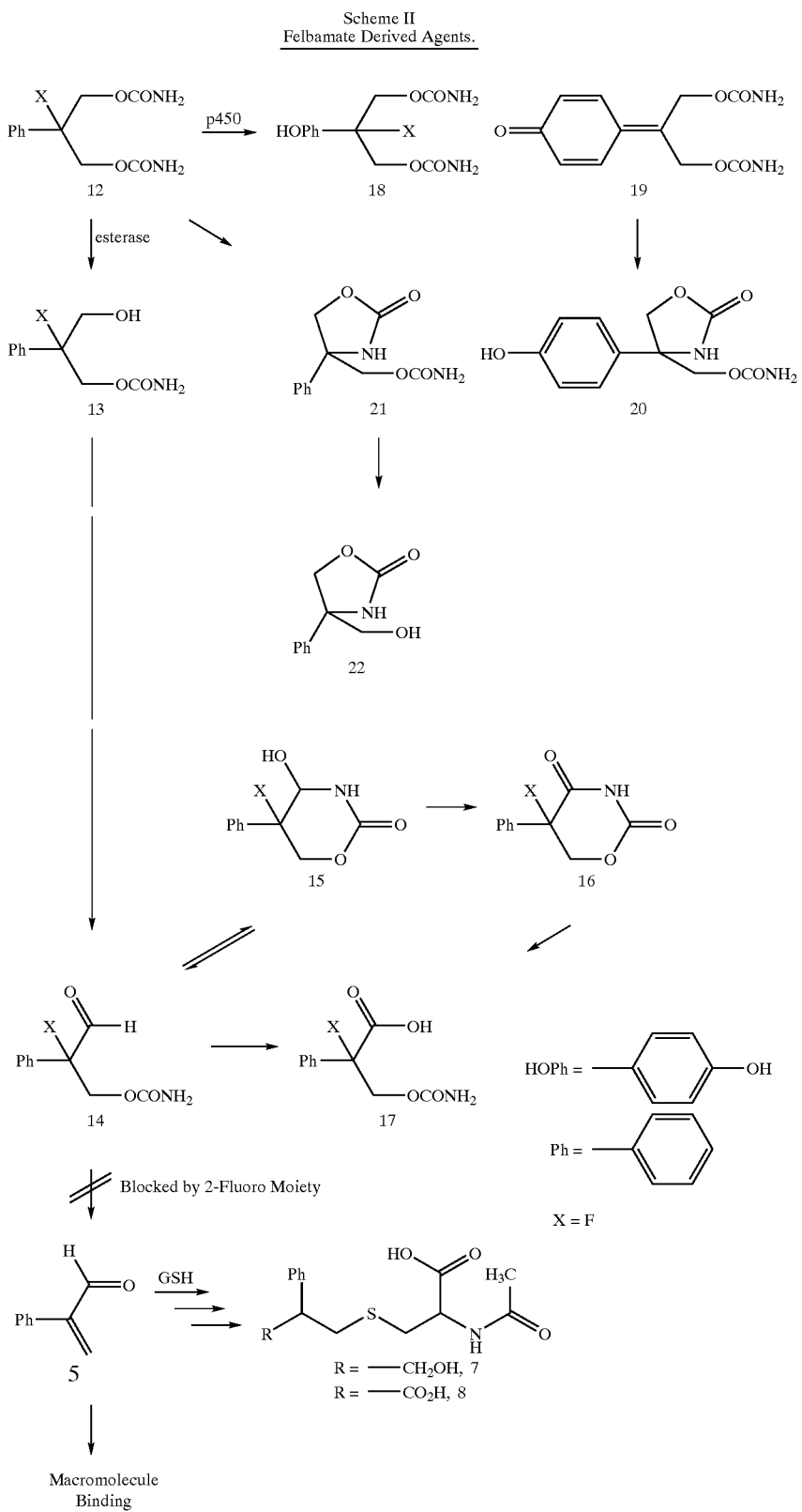

possessing structural similarity to felbamate, will not exhibit felbamate's metabolic profile and will not induce adverse reactions such as those associated with the use of felbamate.

In accordance with one embodiment of the present invention these compounds can be further modified to include substituents at the para position of the benzene ring of the felbamate derivative to preclude the formation of other potentially toxic species via the cytochrome P450 pathway. This potential cytochrome P450 mediated toxicity may be associated with the 2-substituted-2-phenyl-1,3-propanediol-dicarbamate derivatives of the present invention by formation of electrophilic species such as 19, which may also be formed from dihydroxy felbamate, a known metabolite of felbamate. Felbamate derivative compounds that are substituted at the para position are blocked from being metabolized by certain members of the cytochrome P450 metabolic family. For example, two preferred compounds are difluorofelbamate (23) and difluoro monocarbamate felbamate (24). These felbamate derivatives are incapable of being metabolized to atropaldehyde and also are blocked from being metabolized by certain members of the cytochrome P450 metabolic family.

Parafluoro Substituted Derivatives of Felbamate

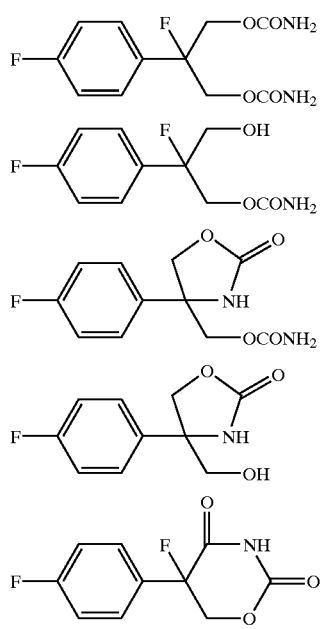

The present invention also encompasses the derivatives of the potentially active metabolites of felbamate. In particular this includes fluoro oxazinane-dione 16 and difluoro oxazinane-dione, which are derivatives of the felbamate metabolite oxazinane-dione 9. The structure of oxazinane-dione 9 bears intriguing similarity to several established anti-epileptic drugs including phenobarbital, phenytoin, oxazinane-dione, metharbital and ethotoin, as illustrated below:

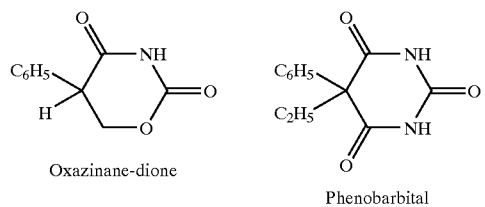

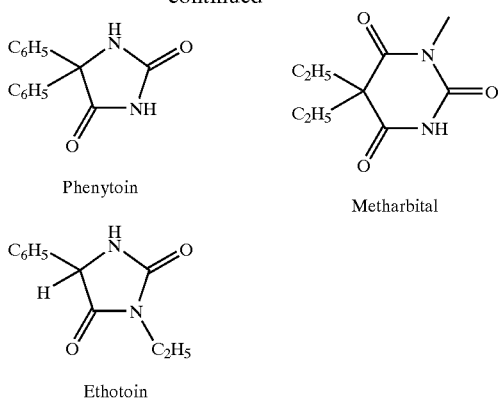

It is anticipated, therefore, that the oxazinane-dione 9 is responsible for some aspects of felbamate's efficacy in vivo. As patients undergoing felbamate therapy for seizure control ingest large quantities of felbamate (grams per day), even a 1–2% conversion to a pharmacologically active metabolite could have significant effects. This could play an important role in the seizure control observed with felbamate, particularly if the metabolite (i.e., the oxazinane-dione) was a more potent compound. In light of the possibility that the oxazinane-dione 9 could be a metabolic precursor to the major human metabolite, acid carbamate 4, it may be formed in significant quantities (the acid carbamate was reported to represent ~12% of a dose). Because the parent oxazinane-dione 9 has been found to be unstable at relevant pH, oxazinane-diones 16 are considered candidates for development as potential antiepileptic agents. Also included in this class are cyclic congeners 21 and 22, which may be formed from felbamate derivatives (see scheme II). Also included is 20, which may be an unknown metabolite of felbamate 1 and could be produced from felbamate derivative 12 by the cytochrome P450 metabolism.

In accordance with one embodiment of the present invention a neurological disorder or localized ischemic event (myocardial or cerebral ischemia) is treated by administering a compound having the general structure:

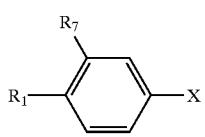

wherein X is selected from the group consisting of

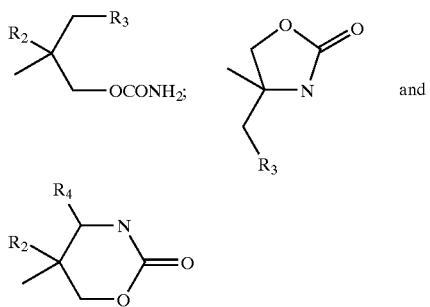

and $R_1$, and $R_7$ are independently selected from the group consisting of H, halo, alkyl, haloalkyl, $-NR_5R_6$, hydroxy, and alkoxy, $R_2$ is Cl or F, $R_3$ is hydroxy or $-OCONH_2$, $R_4$ is hydroxy or carbonyl, $R_5$ and $R_6$ are independently $C_1-C_4$ alkyl.

In an alternative embodiment a neurological disorder or localized ischemic event (myocardial or cerebral ischemia) is treated by administering a compound having the general structure:

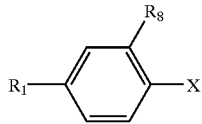

wherein X is selected from the group consisting of

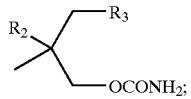
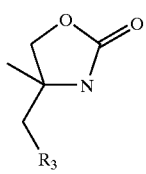
and
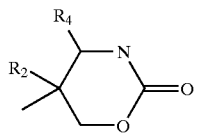

and $R_1$, and $R_8$ are independently selected from the group consisting of H, halo, alkyl, haloalkyl, —$NR_5R_6$, hydroxy, and alkoxy, $R_2$ is Cl or F, $R_3$ is hydroxy or —$OCONH_2$, $R_4$ is hydroxy or carbonyl, $R_5$ and $R_6$ are independently $C_1$–$C_4$ alkyl, is administered to a patient to treat a neurological disorder or myocardial or cerebral ischemia.

In accordance with one embodiment, the compound is selected from the group consisting of

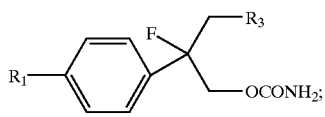
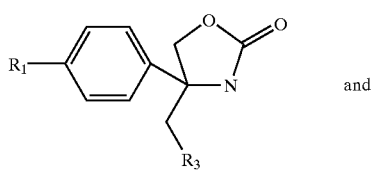
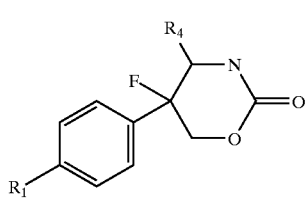

wherein $R_1$ is selected from the group consisting of H, halo, alkyl, haloalkyl, —$NR_5R_6$, hydroxy, and alkoxy, $R_3$ is hydroxy or —$OCONH_2$, $R_4$ is hydroxy or carbonyl, and $R_5$ and $R_6$ are independently $C_1$–$C_4$ alkyl, is administered to a patient to treat a neurological disorder or myocardial or cerebral ischemia.

In accordance with another embodiment the compound is selected from the group consisting of

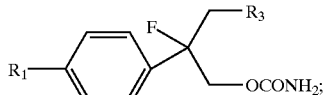
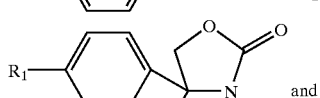
and
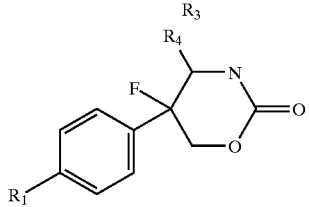

wherein $R_1$ is selected from the group consisting of H or halo, $R_3$ is hydroxy or —$OCONH_2$, and $R_4$ is hydroxy or carbonyl, and in one preferred embodiment the compound is selected from the group consisting of

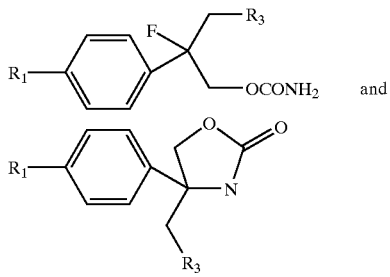
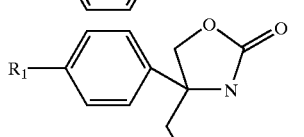
and wherein $R_1$ is selected from the group consisting of H, F, Cl, $CF_3$ and hydroxy and $R_3$ is hydroxy or —$OCONH_2$. In one preferred embodiment $R_1$, is H or F and $R_3$ is —$OCONH_2$.

Compositions comprising the felbamate derivative of the present invention can be used to treat patients suffering from a neurological diseases such as epileptic seizures or can be used to prevent or treat reperfusion injuries resulting from stroke, myocardial infarction, and spinal chord perfusion-type injuries. It is believed that the felbamate derivatives of the present invention also have utility for treating conditions characterized by the presence of reactive oxygen species (ROS).

The felbamate derivative of the present invention can be combined with pharmaceutically acceptable carriers, stabilizing agents, solubilizing agents, and fillers known to those skilled in the art for administration to the patient. The compositions can be formulated using standard delivery vehicles and standard formulations for oral, parenteral or transdermal delivery.

In accordance with one embodiment a patient suffering from a neurological disorder or from a reperfusion injury can be treated with the felbamate derivatives, and/or the metabolites of the felbamate derivatives to alleviate the symptoms associated with said disorder or injury. In accordance with the present invention a method for treating patients suffering from a neurological diseases such as epileptic seizures or for treating reperfusion injuries comprises the steps of administering to the patient a composition comprising a compound is selected from the group consisting of

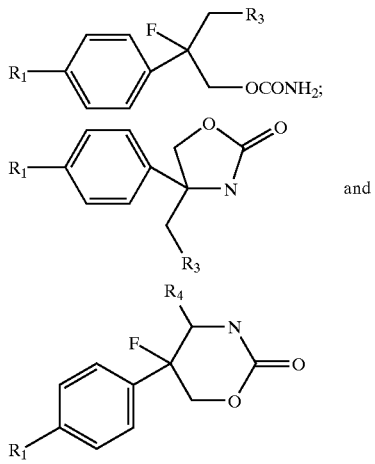

wherein $R_1$ is selected from the group consisting of H, halo, alkyl, haloalkyl and hydroxy, $R_3$ is hydroxy or —$OCONH_2$, and $R_4$ is hydroxy or carbonyl, in combination with a pharmaceutically acceptable carrier. In one preferred embodiment the composition comprises a compound selected from the group consisting of

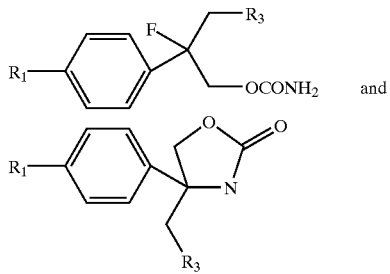

wherein $R_1$ is selected from the group consisting of H, F, Cl, $CF_3$ and hydroxy, $R_3$ is hydroxy or —$OCONH_2$ in combination with a pharmaceutically acceptable carrier.

When administered orally, the compounds can be administered as a liquid solution, powder, tablet, capsule or lozenge. The compounds can be used in combination with one or more conventional pharmaceutical additive or excipients used in the preparation of tablets, capsules, lozenges and other orally administrable forms. When administered as an intravenous solution, the derivatives of the present invention can be admixed with conventional IV solutions.

The compounds of the present invention are administered at a dose range effective to alleviate the symptoms associated with the disorder. In accordance with one embodiment the felbamate derivative (active agent) is administered in a dosage form of about 0.1 mg/kg to about 5.0 g/kg, and more particularly about 0.25 mg/kg to about 1 g/kg. The dosage will vary based on the route of administration and the condition/disorder to be treated.

EXAMPLE 1

Use of an LC/MS method to quantify the two atropaldehyde derived mercaptuic acids 7 and 8 in a patient population treated with felbamate.

Although the FDA has recommended patients be given felbamate therapy only when other therapies have failed, it is estimated that 8,000–12,000 patients remain on felbamate therapy in the United States (12). While the mercapturic acids are generated from addition to glutathione, any similar nucleophile (i.e., nucleophilic amino acids of proteins or DNA bases) would be expected to undergo conjugation to atropaldehyde. The more atropaldehyde generated in vivo the greater the likelihood that a critical target will be alkylated, leading to toxicity. Therefore, it is reasonable to expect that the potential for toxicity will correlate to the amount of atropaldehyde formed. Further, the amount of atropaldehyde derived mercapturic acids excreted in urine will be a function of the amount of atropaldehyde formed.

In accordance with one aspect of the present invention an analytical method is described for quantifying the relevant metabolites excreted in patient urine as a measurement of a patient's susceptibility to toxicity associated with felbamate therapy. The method of determining a patient's susceptibility to adverse side affects from felbamate administration comprises the steps of obtaining a biological sample from the patient, preferably a urine sample, quantifying the mercapturic acid metabolites present in the sample and extrapolating the amount of atropaldehyde formed. In accordance with one embodiment standard liquid chromatography and mass spectroscopy (LC/MS) is used for quantifying the relevant metabolites excreted in patient urine.

Materials and Methods

Chemicals and Instruments. All reagents were purchased from either Aldrich Chemical Co. or Sigma Chemical Co. and were of the highest quality available. HPLC was performed on a Waters 2690 Separations Module with a Waters 484 tunable absorbency detector (at 214 nm) using a Waters Symmetry $C_{18}$ (2.1 mm×150 mm) column. Mass Spectra were obtained by coupling this LC system to a Finnigan MAT LCQ ion trap mass spectrometer equipped with an electrospray ionization source. NMR spectra were recorded on a General Electric QE300 spectrometer at 300 MHz and chemical shifts are reported in ppm. Melting points were determined on a Thomas-Hoover UNI-MELT apparatus and are uncorrected.

Synthesis. 2-Phenyl-(1,1,3,3-tetra-deuterio)-1,3-propanediol. 2-Phenyl-(1,1,3,3-tetra-deuterio)-1,3-propanediol was obtained by reduction of diethyl phenylmalonate with $LiAlD_4$ using methodology described previously for the formation of 2-phenyl-1,3-propanediol (1). The isotopic purity of the product was determined to be ≧98% as assessed by $^1H$ NMR and GC/MS. (mp=48–50° C.) $^1H$ NMR ($CDCl_3$): δ2.6 (s, 2H), 3.0 (s, 1H), 7.3 (m, 5H). $^{13}C$ NMR ($CDCl_3$): δ49.8, 127.7, 128.5, 129.3, 139.9. GC/MS (CI-methane) $MH^+$=157-fragment ions: 139, 121, 106, 93. Elemental Analysis: theoretical C, 69.20; H, 7.74 found C, 68.98; H, 7.68. Molecular mass is calculated with 4 $^2H$ atoms but the instrument used for elemental analysis observes each deuterium as though it were hydrogen. Therefore, the theoretical value for elemental analysis of hydrogen is determined based on the presence of 12 $^1H$ (i.e., 12×1.008=12.096/156.21=7.74%).

2-Phenyl-(I,I,3,3-tetra-deuterio)-1,3-propanediol monocarbamate. The $d_4$-monocarbamate alcohol was prepared from the $d_4$-diol using methodology described previously (1). The isotopic purity of the product was determined to be ≧98% as assessed by $^1H$ NMR and LC/MS. (mp=71–72° C.) $^1H$ NMR (($CD_3$)$_2$CO): δ3.1 (s,1H), 4.8 (bs, 2H), 7.3 (m, 5H). LC/ESI-MS: $MH^+$=200.0.

3-Carbamoyl-(3,3-di-deuterio)-2-phenylpropionic acid. The $d_2$-acid carbamate was obtained essentially as described by Adusumalli et al. except that the $d_4$-monocarbamate alcohol was used as starting material (10). The isotopic purity of the product was determined to be ≧98% as assessed by $^1$H NMR and LC/MS. (mp=99–102° C.) $^1$H NMR ((CD$_3$)$_2$SO): δ3.9 (s, 1H), 5.8 (bs, 2H), 7.3 (m, 5H), 12.4 (bs, 1H). $^{13}$C NMR ((CD$_3$)$_2$CO): δ54.1, 127.3, 128.7, 128.7, 139.3, 155.6, 201.7. LC/ESI-MS: MH$^+$=211.9. Elemental Analysis: theoretical C, 56.87; H, 5.25; N, 6.63 found C, 56.74; H, 5.31; N, 6.57.

2-Phenyl-(1,1,3,3-tetra-deuterio)-1,3-propanediol dicarbamate. d$_4$-Felbamate was made using methodology described previously except that d$_4$-monocarbamate alcohol was used as starting material (2). The isotopic purity of the product was determined to be ≧98% as assessed by $^1$H NMR and LC/MS. The spectral data obtained for this compound are in agreement with published values (11). (mp=148–150° C.) $^1$H NMR ((CD$_3$)$_2$SO): δ3.1 (s, 1H), 6.4 (bs, 4H), 7.2 (m, 5H). LC/ESI-MS: MH$^+$=243.1. Elemental Analysis: theoretical C, 54.53; H, 5.83; N, 11.56 found C, 54.63; H, 5.84; N, 11.64.

N-d$_3$-acetyl-L-cysteine. Acetic anhydride (d$_6$) (0.29 g, 2.7 mmol) was added to a solution of Cys(trt)-OH in 20 mL DMF and 1 mL pyridine and stirred overnight. The reaction mixture was diluted with 50 mL ether and extracted with saturated aqueous lithium bromide (2×50 mL). The organics were dried over sodium sulfate and the solvent was removed under reduced pressure. This intermediate was purified by flash chromatography using 1:1 methanol and chloroform affording a white solid: $^1$H NMR (CDCI$_3$) δ7.37–7.12 (m, 15H), 4.13 (m, 1H), 2.60 (m, 2H). The sulfide was deprotected using a solution of TFA in dichloromethane (1:1) for 2 hr. The solvents were removed under reduced pressure and the crude product was used in the next reaction.

N-d$_3$-acetyl-S-(2-phenylpropan-3-ol)-L-cysteine. The d$_3$-Nac-alcohol was formed using methodology described previously except that N-d$_3$-acetyl-cysteine was used in the formation of the d$_3$-Nac-atropaldehyde intermediate (2). The isotopic purity of the product was determined to be ≧95% as assessed by $^1$H NMR and LC/MS. $^1$H NMR (D$_2$O): δ2.66–3.0 (m, 6H), 3.74 (t, 1H, J=5.4 Hz), 4.4 (m, 1H), 7.3 (m, 5H). LC/MS: MH$^+$=301.3.

N-d$_3$-acetyl-S-(2-phenylpropanoic acid)-L-cysteine. The d$_3$-Nac-acid was formed using methodology described previously except that N-d$_3$-acetyl-cysteine was used in the reaction with 2-phenyl acrylic acid (2). The isotopic purity of the product was determined to be ≧95% as assessed by $^1$H NMR and LC/MS. $^1$H NMR (D$_2$O): δ2.75–3.23 (m, 4H), 3.82 (t,1H, J=5.5 Hz), 4.4 (m, 1H), 7.32 (m, 5H). LC/ESI-MS: MH$^+$=315.2.

Preparation of Patient Urine Samples. Urine samples were obtained from patient volunteers undergoing felbamate therapy for control of epileptic seizures and under the care of physicians at either the University of Virginia (Charlottesville, Va.) or the EpiCare Center (Memphis, Tenn.). Urine samples were diluted four fold with distilled water (this was done prior to overnight shipment for samples requiring shipping) and placed in an orbital shaking water bath for 20 min at 37° C. to insure that all of the analytes were in solution. 500 μL of this diluted sample were removed and added to 100 μL of a mixture of the four deuterated internal standards. The concentration of standards in the mixture resulted in the addition of 563 nmol d$_4$-felbamate, 140 nmol d$_2$-acid carbamate, 54.0 nmol d$_3$-Nac-alcohol, and 27.5 nmol d$_3$-Nac-acid to each 500 μL diluted urine sample. After mixing, 200 μL were removed and added to 20 μL of 20% HOAc. This acidified sample was then applied to a preconditioned Waters "Oasis" solid phase extraction cartridge (Waters Corp., Woburn, Mass.). The cartridge was washed with 2 mL 0.1% HOAc followed by 3 mL 10% CH$_3$CN/90% water (0.1%) HOAc. The analytes and internal standards were then eluted with 3 mL 30% CH$_3$CN:70% (0.1%) HOAc. This fraction was then analyzed by LC/MS without further manipulation.

LC/MS Analysis of Urine Samples for Metabolite Quantification. LC/MS analysis was performed using a Waters 2690 HPLC equipped with an autosampler and a Waters 486 tunable absorbency detector. This LC system was interfaced to a Finnigan MAT LCQ ion trap mass spectrometer. A 10 μL injection of the fraction from solid phase extraction was applied to a Waters Symmetry C$_8$ reversed phase column (33% CH$_3$CN:67% (0.1%) HOAc, 2.1 mm×150 mm, 0.2 mL/min). The post-column flow was directed through a Waters 486 tunable absorbency detector (10 μL flow cell, λ=214 nm) which was used for qualitative assessment of the sample and not for quantitation. The flow was then directed to the electrospray ionization source of the LCQ.

The mass spectrometer was programmed to collect data in full scan mode from 190–320 m/z and was tuned to maximize the signal from the analytes under the HPLC conditions. The values for the electrospray parameters were as follows: heated capillary temperature=180° C.; spray voltage=5.6 kV; capillary voltage=20 V; sheath gas (nitrogen) flow rate=70; auxiliary gas (helium) flow rate=20. The automatic gain control (AGC) was on with a target ion count of 7×10$^7$ ions and a maximum ion inject time of 150 ms. The scan time was ~0.5 s. Linear response curves were observed for each analyte and internal standard pair over approximately two orders of magnitude range centered on the absolute amount of each internal standard added to the samples. The amount of analytes in the patient urine samples fell within these linear response ranges.

Quantification was achieved by integration of the peaks from the mass chromatogram for each analyte using software (Navigator 1.1) provided with the LCQ. The area (expressed as counts×seconds) of the peak for each metabolite was compared to the area for its corresponding deuterated internal standard. As the absolute amount of internal standard added per mL of urine was known, the absolute amount of analyte per mL of urine could be determined.

Results

Analysis was performed on 34 urine samples from 31 patients undergoing felbamate therapy for control of epileptic seizures. As is common for epileptics, many of these patients (n=19) were undergoing polytherapy for seizure control with the remainder (n=12) undergoing felbamate monotherapy. The age of this patient pool (14 men and 17 women) spanned from 10–57 years old with a mean age of 37. All of the urine samples analyzed were found to contain both of the mercapturic acids, indicating that formation of atropaldehyde in vivo does occur in the patient population and appears to be universal. More Nac-alcohol 7 was excreted than Nac-acid 8 for all of the patients. The average ratio of Nac-alcohol to Nac-acid was 6.4, however the values varied widely (ratios=2–14).

The absolute amounts of the analytes excreted per mL of urine varied considerably between patients. For example, the amount of felbamate excreted ranged from 819±8.5 nMoles/mL (this patient had a total daily dose of 3.6 grams of felbamate) to 10,064±515 nMoles/mL (this patient had a total daily dose of 6.0 grams of felbamate). This illustrates the effect of urine volume on the results obtained from this method. Though the dosage difference was less than double, the difference in amount of felbamate excreted per mL was greater than ten times. Thus, to compare the results from one patient to another, the values for the metabolites were normalized to the amount of felbamate.

Discussion

We have developed an isotope-dilution based LC/MS method to quantify the amounts of felbamate 1, the acid carbamate 4, and the two mercapturic acids 7 and 8 excreted in patient urine. Although the FDA has recommended patients be given felbamate therapy when other therapies have failed, it is estimated that 8,000–12,000 patients remain on felbamate therapy in the United States (12).

Scheme I illustrates the metabolic pathway leading to atropaldehyde formation and its disposition. The aldehyde carbamate represents the "commitment" step. It is at this point that a molecule is either committed to the toxic pathway of atropaldehyde 5 or the detoxification pathway of the acid carbamate 4. The amount of mercapturic acids 7 and 8 excreted in urine will mirror the flux through the "toxic" pathway. That is, an individual that generates high levels of atropaldehyde would be expected to have correspondingly high levels of the mercapturic acids. Therefore, the ratio of acid carbamate excreted compared to the combined mercapturic acids would describe the disposition of the aldehyde carbamate for a given patient. The values for the two mercapturic acids can be combined as they both represent the same pathway of aldehyde carbamate disposition. Of course, there are other factors that may modulate the disposition through these two pathways (i.e., co-administration of modulators of enzyme activity or glutathione levels), but this appears to be a promising approach to evaluating the metabolic distribution between toxic and non-toxic pathways in a patient population.

We applied this LC/MS method to the analysis of 34 urine samples from 31 patients undergoing felbamate therapy for control of epileptic seizures. All of these patients have been undergoing felbamate therapy for several years, without any of the severe side effects. As the severe toxicities associated with felbamate demonstrate a mean onset time of $\leq 6$ months, these patients probably constitute a population of "normal" or "safe" metabolizers of felbamate.

The data obtained from the urine samples is illustrated that there is a "normal" range for the distribution of the aldehyde carbamate between the acid carbamate and atropaldehyde (as represented by the mercapturic acids). There does not appear to be a significant correlation between sex or therapy type and the relative amounts of metabolites formed. An individual with high esterase activity would produce relatively more of the monocarbamate alcohol from felbamate leading to increased generation of all subsequent metabolites. However, the ratio of the metabolites may still be very similar.

By our hypothesis, alkylation of proteins by atropaldehyde may result in the generation of antigens that precipitate an immune response in a manner similar to mechanisms of immune mediated toxicity for other agents. If the toxicity due to atropaldehyde is immune mediated, then susceptibility to this toxicity will be a function not only of the formation of atropaldehyde-protein conjugates but also of a patient's immune system phenotype. Some patients may have a particular phenotype that makes them allergic to atropaldehyde-protein conjugates while others do not exhibit this response. Alternatively, everyone may have the potential for an immune response, but the amount of atropaldehyde protein conjugates produced must reach a critical level before the immune response occurs. That is, all of the patients may be producing low levels of antigens, but the levels are not normally high enough to trigger an immune response. It is not until a secondary event, such as inhibition of acid carbamate formation or glutathione depletion, occurs that the production of antigens surpasses the critical level and toxicity is manifest.

Because of the potential for an immune mediated component for felbamate toxicity by our hypothesis, it may be important to understand both an individual's level of atropaldehyde formation and their phenotype to develop a complete screening method. The method described above has demonstrated sufficient precision for the identification of "outliers" and appears to hold potential for the monitoring of patients undergoing felbamate therapy.

EXAMPLE 2

Synthesis of Felbamate Derivatives

Materials and Methods

Chemicals and Instruments. All reagents were purchased from Aldrich Chemical Co. and were of the highest quality available. HPLC was performed on a Waters 2690 Separations Module with a Waters 484 tunable absorbency detector (at 214 nm) using a Waters Symmetry $C_{18}$ (2.1 mm×150 mm) column. Mass Spectra were obtained by coupling this LC system to a Finnigan MAT LCQ ion trap mass spectrometer equipped with an electrospray ionization source. NMR spectra were recorded on a General Electric QE300 spectrometer at 300 MHz and chemical shifts are reported in ppm. Melting points were determined on a Thomas-Hoover UNI-MELT apparatus and are uncorrected.

Synthesis

2-Fluoro-2-phenyl-1,3-propanediol. 2-Fluoro-2-phenyl-1,3-propanediol was obtained from diethyl 2-fluoro-2-phenylmalonate by lithium aluminum hydride reduction using methodology analogous to that described previously for the formation of 2-phenyl-1,3-propanediol. (Thompson etal., *Chem. Res. Toxicol.* 9, 1225–1229 (1996)). However, the reduction was initiated at −40° C. and was allowed to warm to room temperature over one hour, followed by stirring for an additional 1 to 2 hours, at which time the reaction was complete by TLC. $^1$H NMR (CDCl$_3$): δ7.43–7.3 (m, 5H), 4.01 (dq, 4H, J=22.7, 12.3 Hz), 2.82 (bs, 2H), $^{13}$C NMR (CDCl$_3$): 138.2, 129.1, 129.1, 128.9, 125.3, 125.2, 100.4, 98.0, 67.0, 66.7.

2-Fluoro-2-phenyl-1,3-propanediol monocarbamate (13, x=Fluoro). The title compound was prepared from the 2-fluoro-2-phenyl-1,3-propanediol using methodology described previously. (Thompson etal., *Chem. Res. Toxicol.* 9, 1225–1229 (1996)). The product thus obtained was recrystalized from ethyl ether and the purity of the product was determined to be 98% as assessed by $^1$H NMR and LC/MS (72% yield, $R_{f(ethyl\ ether)}$=0.25, mp=67–69° C.). $^1$H NMR ((CDCl$_3$): δ7.4–7.2 (m, 5H), 5.05 (bs, 2H), 4.52 (ddd, 2H, J=20.2, 12.5, 6.5 Hz), 3.9 (dd, 2H, J=12.5, 6.5 Hz). LC/ESI-MS: MH$^+$=214.

3-Carbamoyl-2-fluoro-2-phenylpropionic acid (17, x=Fluoro). 3-Carbamoyl-2-fluoro-2-phenylpropionic acid 17 was prepared from 2-fluoro-2-phenyl-1,3-propanediol monocarbamate 13 following the procedure of Adusumalli et al, which describes the preparation of 3-carbamoyl-2-phenylpropionic acid (85% yield, $R_{f(ethyl\ ether)}$=0.05). $^1$H NMR ((CDCl$_3$): δ9.1 (bs, 1H), 7.6–7.2 (m, 5H), 5.4 (bs, 2H), 4.8 (dd, 1H, J=10, 7 Hz), 4.72 (t, 1H, J=7 Hz).

2-Fluoro-2-phenyl-1,3-propanediol dicarbamate (12, x=Fluoro). The title compound, fluoro felbamate 12, was made from 2-fluoro-2-phenyl-1,3-propanediol by the method of Adusumalli et al, which describes the preparation of felbamate *Drug. Metab. Disp.* 21, 710–716 (1993). (82% yield, $R_{f(ethyl\ ether)}$=0.20, mp=69 −72° C.). $^1$H NMR ((CDCl$_3$): δ7.4–7.3 (m, 5H), 5.2 (bs, 4H), 4.48 (dq, 4H, J=20.8, 14.2 Hz). C, 56.33; H, 5.67; N, 6.57 found C, 56.24; H, 5.55; N, 6.52.

5-Fluoro-5-phenyl-1,3-oxazinane-2,4-dione (16, x=Fluoro). 3-carbamoyl-2-fluoro-2-phenyl propionic acid (17, 0.1 mmol) and 1,1'-carbonyldiimidizole (0.25 mmol) were dissolved in dichloromethane (5 mL) and the resultant solution was magnetically stirred for 12 hours in a sealed vessel.[12] The mixture was purified by passage of the crude reaction mixture through a pad of silica gel (10 g) in a fritted funnel, eluting with ethyl ether, affording, after recrystalization from ethyl ether, the title compound as a white powder in 42% yield ($R_{f(ethyl\ ether)}$=0.70, mp=115–117° C.). $^1$H NMR (CDCl$_3$): δ7.48–7.43 (m, 3H), 7.42–7.37 (m, 2H), 4.93 (dd, 2H, J=24.6, 12.7 Hz), 4.68 (t, 2H, J=13 Hz) LC/ESI-MS: MH$^+$=210° C., 57.42; H, 3.85; N, 6.70 found C, 57.23; H, 3.88; N, 6.67.

EXAMPLE 3

Neuroprotection and Toxicity Assays

The fluoro derivatives synthesized were submitted to the National Institute of Neurological Disorders and Stroke (NINDS) for evaluation in a standard panel of assays. Two convulsant tests (MES and scMET), and a toxicity screen (rotorod in mice, positional sense and gait in rats) were employed for evaluating the compounds activity as neuroprotecting agents. These testing procedures are described in detail in *Molecular and Cellular Targets for Anti-epileptic Drugs*, eds. G. Avanzini, G. Regesta, P. Tanganelli, M. Avoli, 1997, John Libbey & Company Ltd, pp 191–198. The felbamate derivatives were evaluated for anticonvulsant activity following intraperitoneal (i.p.) administration in mice and oral administration in rats.

The Maximal Electroshock Seizure (MES)

The MES test is a model for generalized tonic-clonic seizures and is used to identify compounds which prevent seizure spread. The behavioral and electrographic seizures generated in this model are consistent with the human disorder. In the MES test, an electrical stimulus of 0.2 s in duration (50 mA in mice and 150 mA in rat at 60 Hz) was delivered via corneal electrodes primed with an electrolyte solution containing an anesthetic agent. Mice were tested at 30 minutes and 4 hours following doses of 30, 100 and 300 mg/kg of test compound. Rats were tested at time intervals between 0.25 and 4 hours following a standard oral dose of 30 mg/kg. Abolition of the hindlimb tonic extensor component indicates the test compound's ability to inhibit MES-induced seizure spread.

The Subcutaneous (Metrazol) Seizure Test (scMET)

This is a model that primarily identifies compounds that raise seizure threshold. With some minor exceptions, the pharmacological profile of the scMET seizure model is consistent with the human condition. The scMET test utilizes a dose of pentylenetetrazol (85 mg/kg in Carworth Farms No. 1 mice and 70 mg/kg in Sprague-Dawley rats) that induces clonic seizures lasting for a period of at least five seconds in 97% (CD97) of animals tested. At the anticipated time of testing the convulsant is administered subcutaneously. The test compound is administered intraperitoneally in mice and orally in rats. Animals are observed over a 30 minute period. Absence of clonic spasms in the observed time period indicates a compound's ability to abolish the effect of pentylenetetrazol on seizure threshold. All clinically active anticonvulsants have been found to be protective in at least one of these two tests.

Minimal Neurotoxicity

Toxicity induced by a compound is detected in mice using the standardized rotorod test described by Dunham & Miya (1957). Untreated control mice, when placed on a 6 r.p.m. rotation rod, can maintain their equilibrium for a prolonged period of time. Neurological impairment can be demonstrated by the inability of a mouse to maintain equilibrium for one minute in each of three successive trials.

Rats are examined for behavioral toxicity by the positional sense test and a gait and stance test. In the positional sense test, one hind leg is gently lowered over the edge of a table, whereupon the rat, experiencing neurological deficit, will fail to lift its leg quickly back to a normal position. In the gait and stance test, neurotoxicity is indicated by a circular or zigzag gait, ataxia, abnormal spread of the legs, abnormal posture, tremor hyperactivity, lack of exploratory behavior, somnolence, stupor or catalepsy.

Results

The results of these evaluations (MES, scMET and toxicity (TOX)) are summarized in Tables 1–6. For the MES and scMET tests the data is presented in the form of the number of animals protected by the administered compound/total number of animals tested. For the toxicity test, data is presented in the form of the number of animals exhibiting toxic effects/total number of animals tested. Qualitative data was obtained for fluoro felbamate 12 (Tables 1 and 2A), fluoro monocarbamate felbamate 13 (Tables 1 and 2B), and flourodioxo 16 (Tables 1 and 2C) and for cyclic felbamate 21 (Tables 5 and 6B) and cyclic monocarbamate 22 (Tables 5 and 6A). More extensive quantitative data was also obtained for fluoro felbamate 12 in mice (Table 3) and rats (Table 4).

Many of the agents proposed herein are derived from felbamate 1 or it's metabolites and should possess greater metabolic stability than the corresponding parent agents. Fluoro felbamate 12 and fluoro monocarbamate felbamate 13 each show anti-seizure activity and neither appears to exhibit high levels of toxicity. Surprisingly, fluoro felbamate 12 was found to be approximately 5–10 times more active than felbamate.

Fluoro felbamate 12 showed MES protective effects at 30 mg/kg at both 30 minutes and at 4 hours (see Table 1). There are some toxic effects observed at that dosage at the 30 minute timepoint but not at 4 hours. Toxicity across time doe not occur until dosages of 300 mg/kg. As shown in Table 2A, fluoro felbamate 12 provided full protection at 30 mg/kg over several timepoints. Quantitative results obtained for fluoro felbamate 12 in mice indicated a MES ED50 of approximately 20 mg/kg with a safety ratio of at least five (see Table 3). Results obtained for oral administration of fluoro felbamate 12 to rats indicated a MES ED50 of about 3 mg/kg with no toxicity at doses up to 500 mg/kg. Finally, oral administration of fluoro felbamate 12 to mice indicated a MES ED50 of about 27 mg/kg with no toxicity at doses up to 218 mg/kg.

Fluoro monocarbamate felbamate 13 showed moderate MES protection at a dosage of 100 mg/kg in mice (see Table 1). Orally protection is seen at several different timepoints at a dosage level of 30 mg/kg (see Table 2B).

Interestingly, fluoro oxazinane-dione 16 was found to be inactive in mice but possesses strong anti-seizure activity in rats (Tables 1 and 2C). The preliminary evaluation of Cyclic-MCF 22 and Cyclic-Felbamate 21 is summarized in Tables 5, 6A and 6B. These agents also displayed potent activity in rat models.

TABLE 1

Qualitative Evaluation of Fluoro Derivatives in Mouse.

| Mice I. P. | | fluoro felbamate | | fluoro monocarbamate felbamate | | fluoro dioxo | |
|---|---|---|---|---|---|---|---|
| | Dose | Time | | Time | | Time | |
| Test | mg/kg | 0.5 h | 4.0 h | 0.5 h | 4.0 h | 0.5 h | 4.0 h |
| MES | 3 | 0/4 | 0/1 | | | | |
| | 10 | 0/4 | 1/4 | | | | |
| | 30 | 1/1 | 1/1 | 0/1 | 0/1 | 0/1 | 0/1 |
| | 100 | 3/3 | 3/3 | 2/3 | 0/3 | 0/3 | 0/3 |
| | 300 | 1/1 | 1/1 | 1/1 | 0/1 | 0/1 | 0/1 |
| ScMET | 30 | 0/1 | 0/1 | 0/1 | 0/1 | 0/1 | 0/1 |
| | 100 | 0/1 | 0/1 | 0/1 | 0/1 | 0/1 | 0/1 |
| | 300 | 0/1 | 0/1 | 1/1 | 0/1 | 0/1 | 0/1 |
| TOX | 3 | 0/4 | 0/4 | | | | |
| | 10 | 0/4 | 0/4 | | | | |
| | 30 | 1/4 | 0/2 | 0/4 | 0/2 | 0/4 | 0/2 |
| | 100 | 4/8 | 0/4 | 3/8 | 0/4 | 0/8 | 0/4 |
| | 300 | 4/4 | 2/2 | 2/4 | 0/2 | 1/4 | 0/2 |

TABLE 2A

Qualitative Evaluation of Fluoro Derivatives in Rat.

| Rat (p.o.) Dose | | fluoro felbamate Time | | | | |
|---|---|---|---|---|---|---|
| Test | mg/kg | 0.25 h | 0.5 h | 1.0 h | 2.0 h | 4.0 h |
| MES | 30 | 2/4 | 4/4 | 4/4 | 4/4 | 4/4 |
| TOX | 30 | 0/4 | 0/4 | 0/4 | 0/4 | 1/4 |

TABLE 2B

Qualitative Evaluation of Fluoro Derivatives in Rat.

| Rat (p.o.) Dose | | fluoro monocarbamate felbamate Time | | | | |
|---|---|---|---|---|---|---|
| Test | mg/kg | 0.25 h | 0.5 h | 1.0 h | 2.0 h | 4.0 h |
| MES | 30 | 0/4 | 3/4 | 0/4 | 1/4 | 0/4 |
| TOX | 30 | 0/4 | 0/4 | 0/4 | 0/4 | 0/4 |

TABLE 2C

Qualitative Evaluation of Fluoro Derivatives in Rat.

| Rat (p.o.) Dose | | fluoro dioxo Time | | | | |
|---|---|---|---|---|---|---|
| Test | mg/kg | 0.25 h | 0.5 h | 1.0 h | 2.0 h | 4.0 h |
| MES | 30 | 0/4 | 1/4 | 1/4 | 1/4 | 2/4 |
| TOX | 30 | 0/4 | 0/4 | 0/4 | 0/4 | 0/4 |

TABLE 3

Quantitative Evaluation of Fluoro Felbamate in Mouse.

| Test (I.P.) | ED50 (mg/kg) |
|---|---|
| MES | 19.96 |
| ScMET | >160.00 |
| TOX | 115 |

TABLE 4

Quantitative Evaluation of Fluoro Felbamate in Rat.

| Test (p.o.) | ED50 (mg/kg) |
|---|---|
| MES | 3.0 |
| ScMET | >250.00 |
| TOX | >500 |

TABLE 5

Qualitative Evaluation of Fluoro Derivatives in Mouse.

| Mice I. P. Dose | | Cyclic MCF Time | | cyclic felbamate Time | |
|---|---|---|---|---|---|
| Test | mg/kg | 0.5 h | 2.0 h | 0.5 h | 4.0 h |
| MES | 30 | 0/1 | 0/1 | 0/1 | 0/1 |
| | 100 | 0/3 | 2/3 | 0/3 | 0/3 |
| | 300 | 1/1 | 1/1 | 0/1 | 0/1 |
| ScMET | 30 | 0/1 | 0/1 | 0/1 | 0/1 |
| | 100 | 2/5 | 0/1 | 0/1 | 0/1 |
| | 300 | 2/5 | 0/1 | 0/1 | 0/1 |
| TOX | 30 | 0/4 | 0/2 | 0/4 | 0/2 |
| | 100 | 0/8 | 0/4 | 0/8 | 0/4 |
| | 300 | 0/4 | 0/2 | 0/4 | 0/2 |

TABLE 6A

Qualitative Evaluation of Fluoro Derivatives in Rat.

| Rat (p.o.) Dose | | Cyclic MCF Time | | | | |
|---|---|---|---|---|---|---|
| Test | mg/kg | 0.25 h | 0.5 h | 1.0 h | 2.0 h | 4.0 h |
| MES | 30 | 0/4 | 0/4 | 1/4 | 2/4 | 3/4 |
| TOX | 30 | 0/4 | 0/4 | 0/4 | 0/4 | 0/4 |

TABLE 6B

Qualitative Evaluation of Fluoro Derivatives in Rat.

| Rat (p.o.) Dose | | cyclic felbamate Time | | | | |
|---|---|---|---|---|---|---|
| Test | mg/kg | 0.25 h | 0.5 h | 1.0 h | 2.0 h | 4.0 h |
| MES | 30 | 2/4 | 2/4 | 3/4 | 0/4 | 3/4 |
| TOX | 30 | 0/4 | 0/4 | 0/4 | 0/4 | 0/4 |

Discussion

The panel of proposed agents (Scheme II), several of which are structural variants of felbamate 1 and it's metabolites, seeks to address the occurrence of idiosyncratic adverse reactions that have been associated with the use of felbamate 1. The results obtained from the evaluation of five of these agents have demonstrated that these agents possess anti seizure activity and they have not, as of yet, exhibited toxicity at therapeutically relevant doses. As is normal for agents that target neurological disorders, these agents have elicited minor levels of neurotoxicity at high doses, but there appears to exist a reasonable therapeutic index. Additionally, the activity of these agents, specifically fluoro felbamate 12 and fluoro monocarbamate felbamate 13, correlates well with the activity of the unfluorinated parent agents, felbamate 1 and monocarbamate felbamate 2, respectively. The evaluation of Cyclic-MCF 22 and Cyclic-Felbamate 21 also demonstrated these agents to be effective in the attenuation of seizures.

Conclusion

Given the success of the evaluation of fluoro felbamate 12, fluoro monocarbamate felbamate 13, fluoro oxazinanedione 16, Cyclic-MCF 22 and Cyclic-Felbamate 21 this panel of agents represents a new class of neuro-active entities that is designed to preclude the formation of putative toxic species that may be associated with the occurrence of adverse reactions observed with the use of felbamate. Taken as a whole, this proposed panel of agents addresses the presumed relevant metabolic processes, namely metabolism to atropaldehyde and metabolism by certain members of the cytochrome P450 metabolic family.

EXAMPLE 4

The Hippocampal Kindling Model

The hippocampal kindling model can be used to evaluate a compound's ability to affect both the expression and acquisition of focal seizures. The hippocampal kindling paradigm as described by Lothman and Williamson (Lothman, 1994) allows the temporal effects of a drug to be evaluated in a single animal. This procedure requires the surgical placement of bipolar electrodes in the ventral hippocampus of adult male Sprague-Dawley rats. Stage five behavioral seizures are produced by using a stimulus consisting of a 50 Hz, 10 s train of 1 ms biphasic 200 uA pulses delivered every 30 min for 6 hours (12 stimuli per day) on alternating days for a total of 60 stimulations (five stimulus days). Prior to evaluating a candidate's anticonvulsant activity, a drug free control period consisting of supramaximal stimulations are recorded to verify the stability of a stage five generalized seizure.

A single dose of the candidate compound is then administered intraperitoneally (i.p.), 15 min following the last control stimulation. The anticonvulsant activity of the drug is assessed every 30 min for three to four hours starting 15 min after administering the test material. After each stimulation, individual Racine seizure scores and afterdischarge durations are recorded. Rats are used again in drug trials after four to five drug- and stimulus-free days.

In the kindling acquisition study, drugs are tested for their ability to prevent the development of the kindled state in electrode implanted rats. The candidate compound is administered during the kindling procedure and at a predetermined time prior to the electrical stimulus. The dosing interval and the dose of the drug are based on the compound's activity observed in the acute seizure expression studies. Results from drug-treated animals are compared to those of saline-treated rats.

This treatment is repeated on stimulus days two, three, four, and five. After a stimulus-free interval of one week, the effect of prior drug treatment on kindling acquisition is assessed by challenging the animal with the kindling stimulus protocol. The standardized kindling protocol is then carried out with the behavioral seizure score and afterdischarge duration recorded for each rat during three 'retest days'. Saline treated rats are fully kindled at the first stimulation following the one week stimulus-free period. An active compound would be expected to lower behavioral scores and afterdischarge duration compared to saline control rats. The suppression or lengthening of the delay in the acquisition of the kindled response may indicate that the candidate compound can act to prevent the development of seizures. Such compounds could be termed 'antiepileptogenetic'.

Results

The kindled results for fluoro felbamate 12 are presented in Table 7. At a dose of 100 mg/kg a significant drop in seizure score was observed along with a corresponding decrease in afterdischarge duration.

TABLE 7

Hippocampal Kindled Rats
Solvent: MC (M & P, SB) Route: i.p.

| Time (min) | fluoro felbamate Seizure Score ± S.E.M. | Afterdischarge Duration (sec) ± S.E.M. |
|---|---|---|
| Dose: 25 mg/kg | | |
| Control | 4.71 ± 0.18 | 73.14 ± 4.61 |
| 15 | 4.86 ± 0.14 | 77.29 ± 4.91 |
| 45 | 4.57 ± 0.20 | 71.43 ± 5.50 |
| 75 | 4.00 ± 0.69 | 64.43 ± 11.19 |
| 105 | 4.57 ± 0.20 | 70.29 ± 4.85 |
| 135 | 4.43 ± 0.57 | 53.86 ± 9.33 |
| 165 | 4.71 ± 0.18 | 59.29 ± 3.28* |
| 195 | 3.86 ± 0.67 | 54.00 ± 9.62 |
| 225 | 4.00 ± 0.69 | 53.29 ± 9.03 |
| 255 | 4.86 ± 0.14 | 64.00 ± 3.42 |
| Dose: 50 mg/kg | | |
| Control | 5.00 ± 0.00 | 83.71 ± 6.97 |
| 15 | 3.86 ± 0.70 | 67.14 ± 12.39 |
| 45 | 2.86 ± 0.83* | 68.57 ± 20.14 |
| 75 | 3.14 ± 0.83* | 63.00 ± 17.45 |
| 105 | 3.43 ± 0.90 | 60.86 ± 14.93 |
| 135 | 3.71 ± 0.64* | 65.00 ± 13.10 |
| 165 | 2.71 ± 0.97* | 43.14 ± 14.67* |
| 195 | 3.14 ± 0.83 | 52.86 ± 14.59 |
| 225 | 3.00 ± 0.87* | 39.86 ± 10.98* |
| 255 | 2.57 ± 0.72* | 33.29 ± 11.76* |
| Dose: 100 mg/kg | | |
| Control | 5.00 ± 0.00 | 76.00 ± 5.03 |
| 15 | 1.75 ± 0.73* | 40.75 ± 15.74 |
| 45 | 1.50 ± 0.57* | 29.00 ± 10.86* |
| 75 | 1.88 ± 0.67* | 38.63 ± 12.58* |
| 105 | 2.38 ± 0.65* | 53.38 ± 12.59 |
| 135 | 2.00 ± 0.76* | 33.63 ± 12.88* |
| 165 | 2.75 ± 0.65* | 43.38 ± 12.79* |
| 195 | 2.25 ± 0.70* | 45.25 ± 13.33* |
| 225 | 2.50 ± 0.73* | 47.38 ± 14.80 |
| 255 | 2.50 ± 0.65* | 45.38 ± 13.92 |

*Significantly different from control.

Dose Responses

| Dose (mg/kg) | Number Protected/ Number Tested | Seizure Score ± S.E.M. | Afterdischarge Duration (sec) ± S.E.M. |
|---|---|---|---|
| 25 | 0/7 | 4.57 ± 0.20 | 71.43 ± 5.50 |
| 50 | 3/7 | 2.86 ± 0.83* | 68.57 ± 20.14 |
| 100 | 7/8[a] | 1.50 ± 0.57* | 29.00 ± 10.86* |

[a]2/8 toxic
*Significantly different from control.

What is claimed is:

1. A compound represented by the general structure:

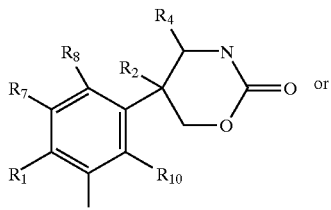 or

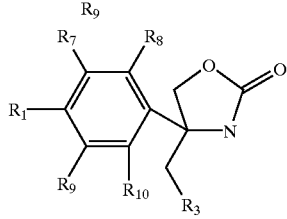

Wherein $R_1$, $R_7$, $R_8$, $R_9$ and $R_{10}$ are independently selected from the group consisting of H, halo, alkyl, haloalkyl, —$NR_5R_6$, hydroxy, and alkoxy;

$R_2$ is F or Cl;

$R_3$ is hydroxy or —$OCONH_2$;

$R_4$ is hydroxy or carbonyl; and $R_5$ and $R_6$ are independently $C_1$–$C_4$ alkyl.

2. The compound of claim 1 wherein
$R_1$, $R_7$ and $R_8$ are independently selected from the group consisting of H, halo, $C_1$–$C_4$ alkyl, $C_1$–$C_4$ haloalkyl and hydroxy;

$R_2$ is F;

$R_3$ is hydroxy or —$OCONH_2$;

$R_4$ is hydroxy or carbonyl; and $R_9$ and $R_{10}$ are both H.

3. The compound of claim 2 wherein $R_1$ is H or halo; and
$R_7$ and $R_8$ are independently selected from the group consisting of H, halo, $C_1$–$C_4$ alkyl, $C_1$–$C_4$ haloalkyl and hydroxy.

4. The compound of claim 3 wherein $R_4$, $R_7$ and $R_8$ are H; and
$R_1$ is H or F.

5. The compound of claim 4 wherein $R_1$ is H and $R_3$ is —$OCONH_2$.

6. The compound of claim 1, wherein the compound is represented by the general structure

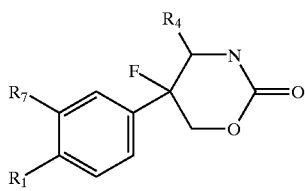

wherein $R_1$ and $R_7$ are independently selected from the group consisting of H, halo and hydroxy; and $R_4$ is hydroxy or carbonyl.

7. The compound of claim 6 wherein $R_7$ is H.

8. The compound of claim 7 wherein $R_1$ is H or F.

9. The compound of claim 1, wherein the compound is represented by the general structure

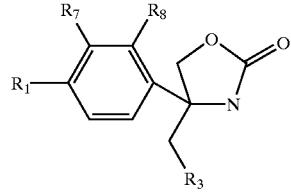

wherein
$R_1$, $R_7$ and $R_8$ are independently selected from the group consisting of H, halo, $C_1$–$C_4$ alkyl, $C_1$–$C_4$ haloalkyl and hydroxy; and $R_3$ is hydroxy or —$OCONH_2$.

10. The compound of claim 9 wherein
$R_1$ is selected from the group consisting of H, F, Cl, $CF_3$ and hydroxy;

$R_3$ is hydroxy or —$OCONH_2$; and $R_7$ and $R_8$ are both H.

11. The compound of claim 10 wherein $R_1$ is H or F.

12. The compound of claim 10 wherein $R_1$ is H or F and $R_3$ is —$OCONH_2$.

13. A method for treating a patient suffering from epileptic seizures said method comprising the step of administering a composition comprising a compound selected from the group consisting of

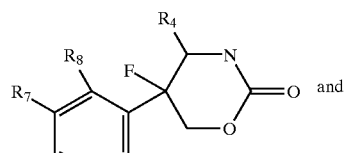 and

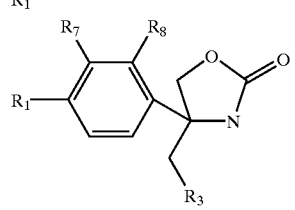

wherein $R_1$, $R_7$ and $R_8$ are independently selected from the group consisting of H, halo, $C_1$–$C_4$ alkyl, $C_1$–$C_4$ haloalkyl and hydroxy;

$R_3$ is hydroxy or —$OCONH_2$; and $R_4$ is hydroxy or carbonyl.

14. The method of claim 13 wherein $R_7$ and $R_8$ are both H.

15. The method of claim 14 wherein $R_1$ is H and $R_3$ is —$OCONH_2$.

16. The method of claim 13 wherein the compound is represented by the general structure

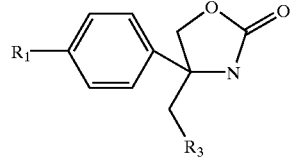

wherein
R₁ is selected from the group consisting of H, F, Cl, CF₃ and hydroxy; and
R₃ is hydroxy or —OCONH₂.

17. The method of claim 16 wherein R₁ is H or F.

18. The method of claim 13 wherein the composition further comprises a pharmaceutically acceptable carrier, and said composition is administered orally.

19. A method for treating a patient suffering from tissue damage resulting from vascular reperfusion or an ischemic event, said method comprising the step of administering a composition comprising a compound selected from the group consisting of

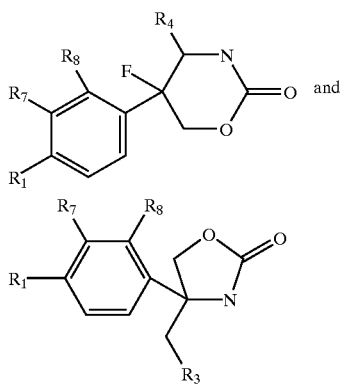

wherein R₁, R₇ and R₈ are independently selected from the group consisting of H, halo, C₁–C₄ alkyl, C₁–C₄ haloalkyl and hydroxy;
R₃ is hydroxy or —OCONH₂; and
R₄ is hydroxy or carbonyl.

20. The method of claim 19 wherein R₇ and R₈ are both H.

21. The method of claim 20 wherein R₁ is H and R₃ is —OCONH₂.

22. The method of claim 19 wherein the composition is administered orally.

23. The method of claim 19 wherein the composition is administered parenterally.

24. A pharmaceutical composition comprising a compound selected from the group consisting of

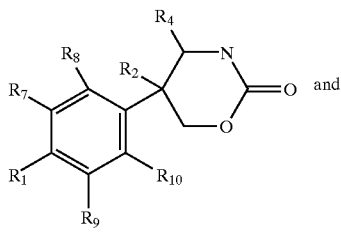

-continued

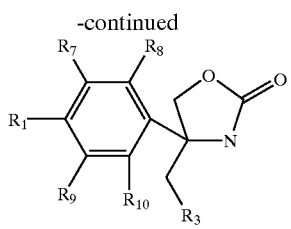

wherein R₁, R₇, R₈, R₉ and R₁₀ are independently selected from the group consisting of H, halo, C₁–C₄ alkyl, C₁–C₄ haloalkyl, —NR₅R₄, hydroxy, and C₁–C₄ alkoxy;
R₂ is F or Cl;
R₃ is hydroxy or —OCONH₂;
R₄ is hydroxy or carbonyl; and
R₅ and R₆ are independently C₁–C₄ alkyl, and a pharmaceutically acceptable carrier.

25. The pharmaceutical composition of claim 24 wherein R₁, R₇ and R₈ are independently selected from the group consisting of H, halo and hydroxy;
R₂ is F;
R₃ is hydroxy or —OCONH₂;
R₄ is hydroxy or carbonyl, and
R₉ and R₁₀ are both H.

26. The pharmaceutical composition of claim 25 wherein R₁ is H or halo; and
R₇ and R₈ are independently selected from the group consisting of H, halo and hydroxy.

27. The pharmaceutical composition of claim 26 wherein R₇ and R₈ are H; and
R₁ is H or F.

28. The pharmaceutical composition of claim 27 wherein R₁ is H and R₃ is —OCONH₂.

29. The pharmaceutical composition of claim 24 wherein said compound has the general structure

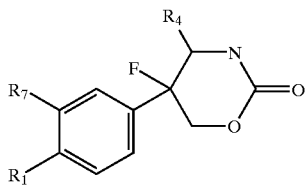

wherein R₁ and R₇ are independently selected from the group consisting of H, halo and hydroxy.

30. The pharmaceutical composition of claim 29 wherein R₇ is H and R₁ is H or F.

* * * * *